US012364836B2

(12) United States Patent
Yamanaka et al.

(10) Patent No.: US 12,364,836 B2
(45) Date of Patent: Jul. 22, 2025

(54) CPAP DEVICE WITH SEALING MEMBER BETWEEN TWO DETACHABLE UNITS

(71) Applicant: Murata Manufacturing Co., Ltd., Kyoto (JP)

(72) Inventors: Yoshio Yamanaka, Kyoto (JP); Yoshihide Amagai, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 702 days.

(21) Appl. No.: 17/650,138

(22) Filed: Feb. 7, 2022

(65) Prior Publication Data

US 2022/0152335 A1 May 19, 2022

Related U.S. Application Data

(63) Continuation of application No. PCT/JP2020/019895, filed on May 20, 2020.

(30) Foreign Application Priority Data

Aug. 8, 2019 (JP) .................................. 2019-146197

(51) Int. Cl.
*A61M 16/08* (2006.01)
*A61M 16/00* (2006.01)
(Continued)

(52) U.S. Cl.
CPC ........ *A61M 16/08* (2013.01); *A61M 16/0003* (2014.02); *A61M 16/0066* (2013.01);
(Continued)

(58) Field of Classification Search
CPC ............ A61M 16/006; A61M 16/0063; A61M 16/0066; A61M 16/08; A61M 16/0816;
(Continued)

(56) References Cited

U.S. PATENT DOCUMENTS 3,064,853 A * 11/1962 Lents ..................... F16J 15/062
220/806
3,275,344 A * 9/1966 Kendt ................. F16L 27/1025
285/260
(Continued)

FOREIGN PATENT DOCUMENTS

AT 000536 U1 * 12/1995
JP H06-012244 U 2/1994
(Continued)

OTHER PUBLICATIONS

International Search Report for PCT/JP2020/019895 dated Jun. 23, 2020.
Written Opinion for PCT/JP2020/019895 dated Jun. 23, 2020.

*Primary Examiner* — Kathryn E Ditmer
(74) *Attorney, Agent, or Firm* — McDonald Hopkins LLC

(57) ABSTRACT

A blower is disposed in a main flow passage of a main unit of a CPAP device. An upstream flow passage connected upstream of the main flow passage is in a base unit. A sealing member secured to the base unit of the CPAP device has an annular shape surrounding a second outlet from outside. The shape of an opening of the sealing member at a distal end edge in the extending direction is a shape surrounding a first inlet from outside. The dimension of the sealing member in the extending direction is greater than the dimension of the sealing member in the thickness direction. When the main unit is attached to the base unit, the dimension of the sealing member in the extending direction is greater than a minimum distance from a proximal end of the sealing member in the extending direction to the main unit.

21 Claims, 7 Drawing Sheets

(51) Int. Cl.
*A61M 16/06* (2006.01)
*A61M 16/16* (2006.01)

(52) U.S. Cl.
CPC .......... *A61M 16/022* (2017.08); *A61M 16/06* (2013.01); *A61M 16/16* (2013.01); *A61M 2016/0027* (2013.01); *A61M 2016/003* (2013.01); *A61M 2205/0216* (2013.01); *A61M 2205/3331* (2013.01); *A61M 2205/3368* (2013.01); *A61M 2205/8206* (2013.01)

(58) Field of Classification Search
CPC ... A61M 16/0875; A61M 16/16; A61M 39/10
See application file for complete search history.

(56) References Cited

U.S. PATENT DOCUMENTS

| | | | |
|---|---|---|---|
| 7,726,309 B2 * | 6/2010 | Ho | A61M 16/0633 128/912 |
| 2004/0237244 A1 | 12/2004 | Suzuki et al. | |
| 2005/0066964 A1 * | 3/2005 | Bathe | A61M 16/08 128/200.14 |
| 2007/0169776 A1 | 7/2007 | Kepler et al. | |
| 2009/0107505 A1 * | 4/2009 | Kleinschmidt | A61M 16/22 128/205.28 |
| 2009/0120434 A1 * | 5/2009 | Smith | A61M 16/0075 128/202.13 |
| 2011/0308518 A1 | 12/2011 | McGroary et al. | |
| 2013/0174843 A1 * | 7/2013 | Smith | A61M 16/16 128/203.26 |
| 2018/0043125 A1 * | 2/2018 | Bencke | F16L 37/086 |
| 2018/0110944 A1 * | 4/2018 | Dai | A61M 16/16 |
| 2018/0200463 A1 * | 7/2018 | Liu | A61M 16/0066 |
| 2021/0372666 A1 * | 12/2021 | Chen | A61M 16/1005 |

FOREIGN PATENT DOCUMENTS

| | | | | |
|---|---|---|---|---|
| JP | H08-013594 A | | 1/1996 | |
| JP | 2004-345715 A | | 12/2004 | |
| JP | 2009-508647 A | | 3/2009 | |
| JP | 2012-517850 A | | 8/2012 | |
| WO | WO-2014147675 A1 | * | 9/2014 | ........ A61M 16/0069 |

* cited by examiner

CPAP DEVICE WITH SEALING MEMBER BETWEEN TWO DETACHABLE UNITS

CROSS REFERENCE TO RELATED APPLICATIONS

This is a continuation of International Application No. PCT/JP2020/019895 filed on May 20, 2020 which claims priority from Japanese Patent Application No. 2019-146197 filed on Aug. 8, 2019. The contents of these applications are incorporated herein by reference in their entireties.

BACKGROUND ART

Technical Field

The present disclosure relates to a continuous positive airway pressure (CPAP) device that feeds air having been sucked into the device to the airway of a user.

A CPAP device as described in Patent Document 1 is used for feeding a fluid to the airway of a user for treatment relating to sleep such as an obstructive sleep apnea syndrome (OSA). The CPAP device includes a blower incorporating a fan and supplies the fluid from the blower to a mask attached to the mouth or nose of the user at a higher pressure than the atmospheric pressure to open the airway.

The CPAP device described in Patent Document 1 includes a unit incorporating the blower and a unit incorporating a humidifier. The unit incorporating the blower is attached to the unit incorporating the humidifier so as to be usable together with the unit incorporating the humidifier. In a state in which the two units are attached, flow passages of air defined in the respective units communicate with each other.

Patent Document 1: Japanese Unexamined Patent Application Publication (Translation of PCT Application) No. 2012-517850

BRIEF SUMMARY

When the CPAP device as described in Patent Document 1 is used in a state in which the two units are attached, each of the units is positioned so that the flow passages of the units can be connected to each other. However, it is difficult for the two units to be correctly positioned and attached. In addition, even when each of the units is positioned, there is a possibility of the air leaking between the flow passages of the units depending on the shape of each of the units and a surface state of a connection portion between the units.

In order to solve the above-described problem, according to an aspect of the present disclosure, a continuous positive airway pressure (CPAP) device feeds air having been introduced thereinto to an airway of a user and includes a first unit and a second unit. The first unit includes a main flow passage through which the air flows and a blower which is disposed in the main flow passage. The second unit includes an upstream flow passage to be connected upstream of the main flow passage and allows the first unit to be detachably attached thereto. A sealing member for sealing a connection portion between the main flow passage and the upstream flow passage is secured to one of the first unit and the second unit. When a unit out of the first unit and the second unit to which the sealing member is secured is defined as a secured-side unit and a unit out of the first unit and the second unit to which the sealing member is not secured is defined as a partner-side unit, in a case where the first unit is attached to the second unit, the sealing member has an annular shape that surrounds an opening of a flow passage of the secured-side unit from outside, and a distal end side of the sealing member in an extending direction extends toward the partner-side unit, in the case where the first unit is attached to the second unit, a shape of an opening at a distal end edge of the sealing member in the extending direction has a shape that is able to surround an opening of a flow passage of the partner-side unit from outside, a dimension of the sealing member in the extending direction is greater than a dimension of the sealing member in a thickness direction, and, in the case where the first unit is attached to the second unit, the dimension of the sealing member in the extending direction is greater than a minimum distance from a proximal end of the sealing member in the extending direction to the partner-side unit.

With the above-described configuration, in the state in which the first unit is attached to the second unit, when the blower of the first unit is driven, due to the flow of the air flowing from the upstream flow passage of the second unit to the main flow passage of the first unit, the pressure in these flow passages becomes a negative pressure relative to the atmospheric. Due to this negative pressure, the sealing member deforms so as to seal a gap between the first unit and the second unit. Accordingly, in the state in which the blower is driven, leakage of the air between the first unit and the second unit can be suppressed.

In the state in which the blower of the CPAP device is driven, ease of suppressing leakage of the air between the flow passages of the first unit and the second unit increases.

DETAILED DESCRIPTION

Hereinafter, an embodiment of a continuous positive airway pressure (CPAP) device that feeds air having been introduced thereinto to the airway of a user is described with reference to the drawings. First, a schematic configuration of the CPAP device is described.

Figure 1:
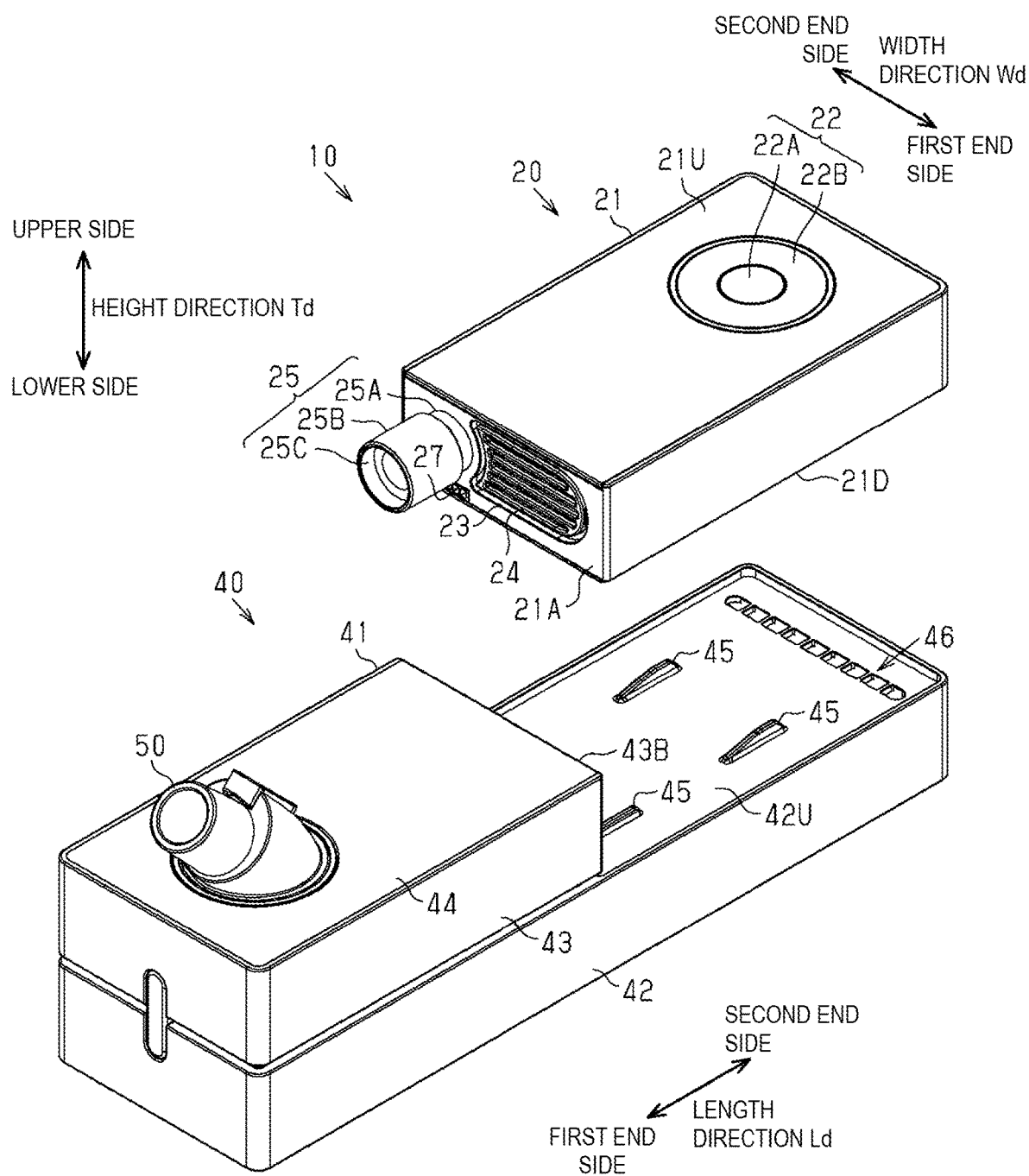
FIG. 1 is a perspective view illustrating a first unit and a second unit of a continuous positive airway pressure (CPAP) device.
Figure 3:
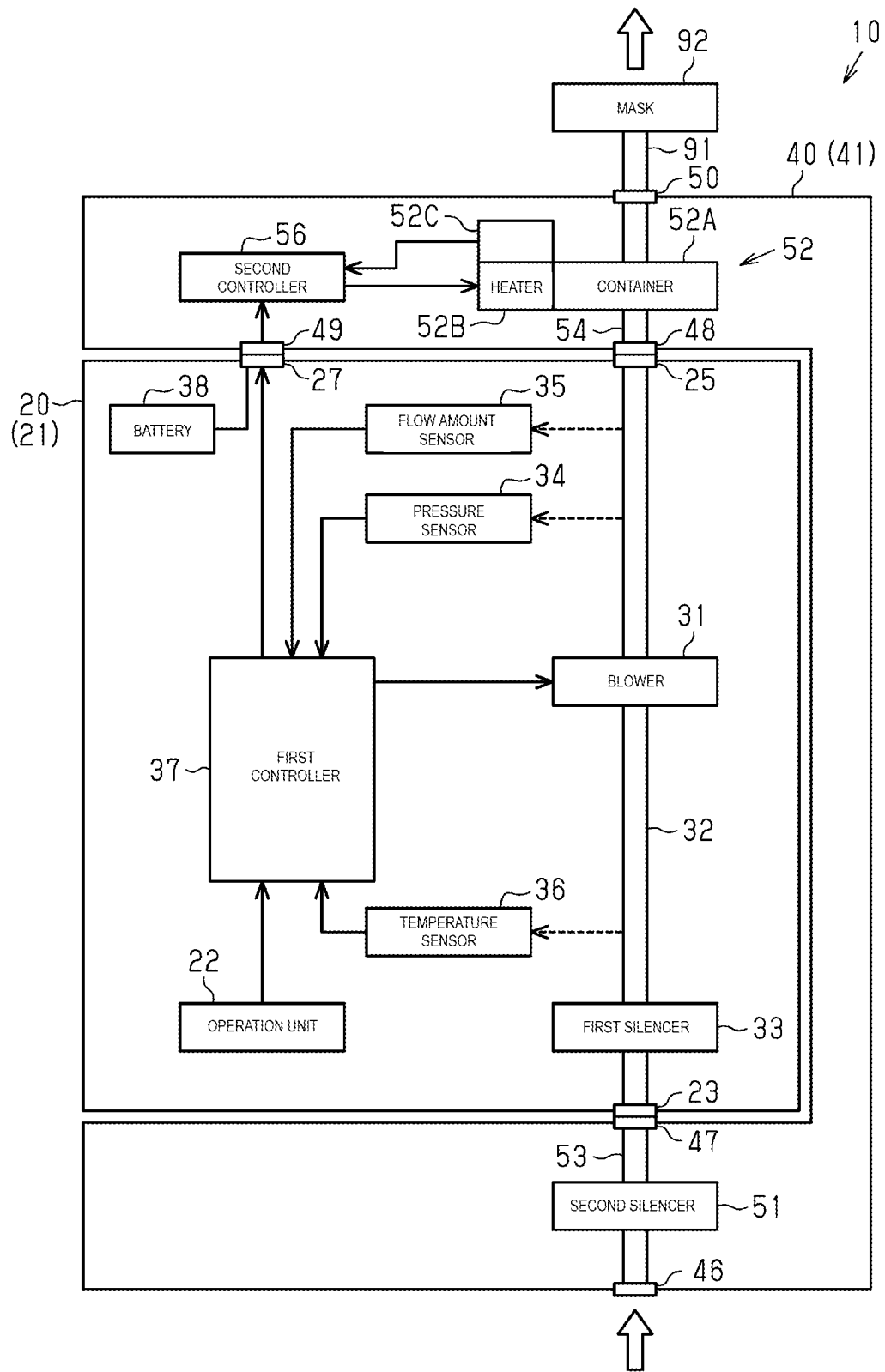
FIG. 3 is an explanatory view illustrating a schematic configuration of the CPAP device in the first use state.

As illustrated in FIG. 1, a CPAP device 10 includes a main unit 20 serving as a first unit and a base unit 40 serving as a second unit. Furthermore, as illustrated in FIG. 3, the main unit 20 includes a blower 31 as a main element. The base unit 40 includes a second silencer 51 and a humidifier 52 as main elements.

Figure 2:
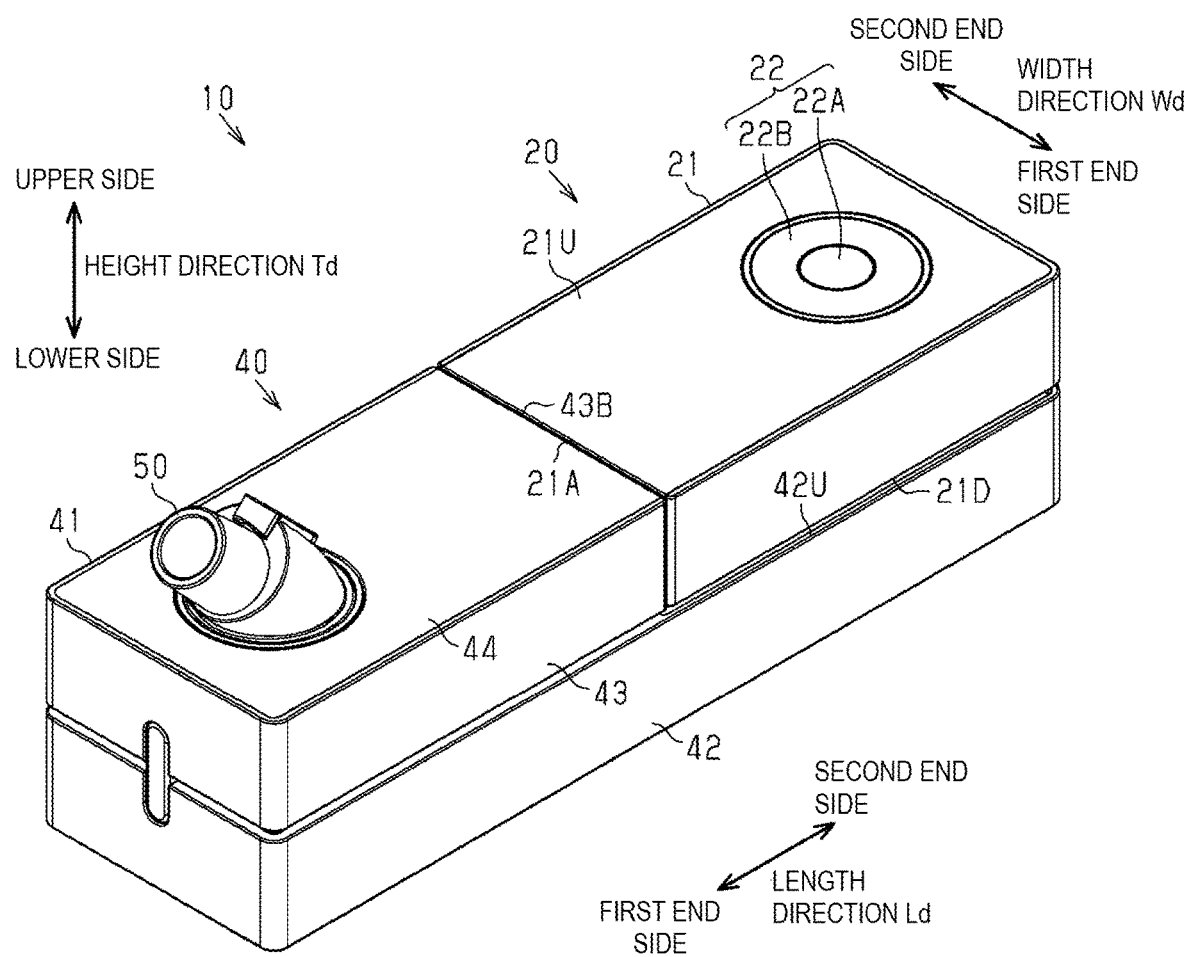
FIG. 2 is a perspective view illustrating the first unit and the second unit of the CPAP device in a first use state.
Figure 4:
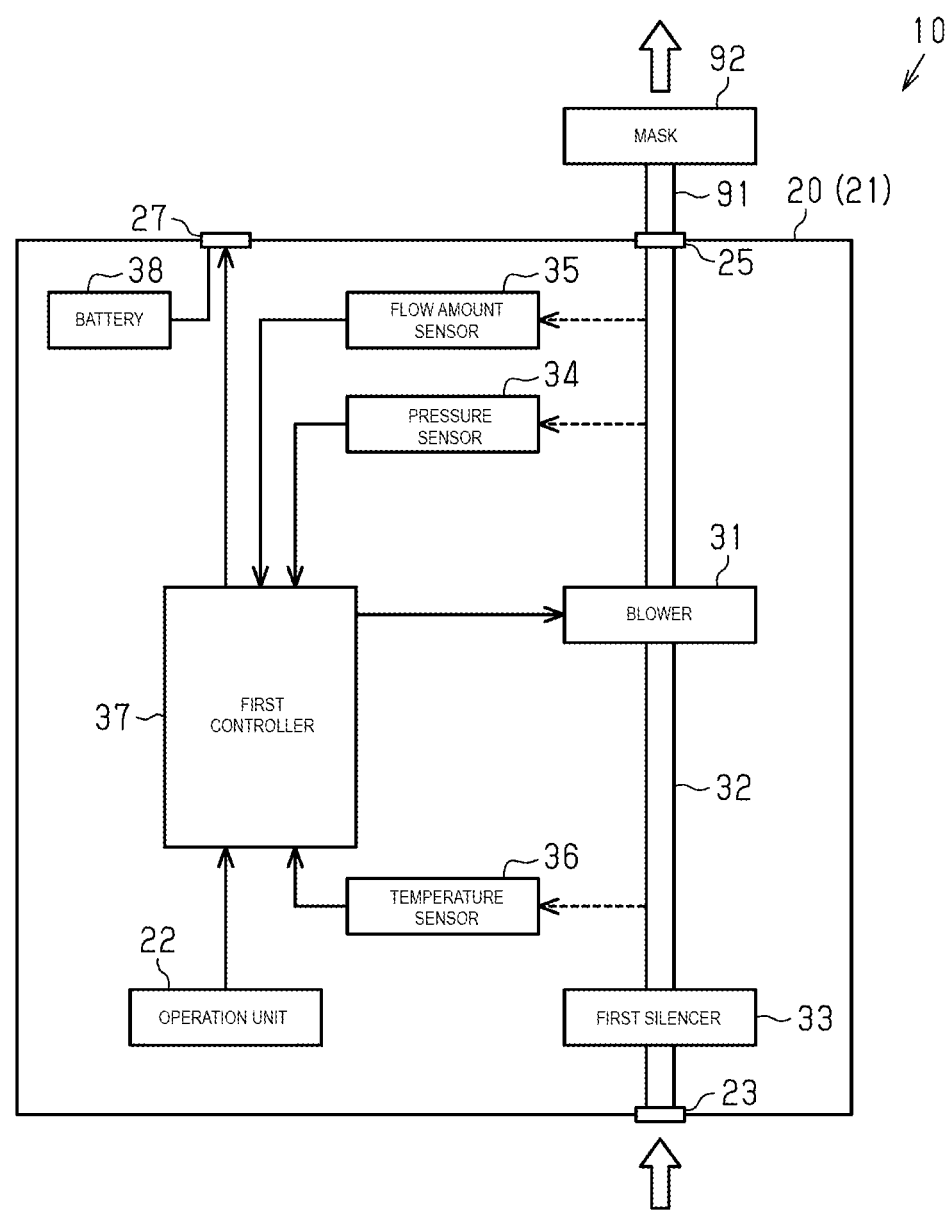
FIG. 4 is an explanatory view illustrating a schematic configuration of the CPAP device in a second use state.

As illustrated in FIGS. 1 and 2, the main unit 20 is detachably attachable to the base unit 40. According to the present embodiment, the CPAP device 10 is configured to be usable in a first use state and a second use state. The first use state is a state in which the main unit 20 is attached to the base unit 40 for use, and the second use state is a state in which the main unit 20 is not attached to the base unit 40 for use. In other words, as illustrated in FIG. 3, both the main unit 20 and the base unit 40 are used in the first use state. As illustrated in FIG. 4, in the second use state, only the main unit 20 is used while the base unit 40 is not used.

Next, the configuration of the main unit 20 is described.

As illustrated in FIG. 1, the main unit 20 includes a first housing 21 having a flat box shape. As illustrated in FIG. 4, the first housing 21 incorporates the blower 31 and so forth disposed in the first housing 21. In the following description, to represent the directions of the first housing 21, as illustrated in FIG. 1, the thickness direction of the first housing 21 is defined as a height direction Td. Furthermore, the long-side direction of the first housing 21 is defined as a length direction Ld, and the narrow-side direction of the first housing 21 is defined as a width direction Wd.

As illustrated in FIG. 1, an operation unit 22 for operating the main unit 20 is provided in an upper surface 21U of the first housing 21. According to the present embodiment, the operation unit 22 includes a switch 22A having a circular shape and a switch 22B having an annular shape disposed so as to surround the switch 22A. Both the switches 22A and 22B are push-button switches and to be operated so as to allow, for example, turning on/off of power of the main unit 20 and changes in setting.

A first inlet 23 for introducing the air from the outside to the inside of the first housing 21 is open in a first end surface 21A, which is an end surface on a first end side in the length direction Ld of the first housing 21. A filter 24 that filters out dust and the like contained in the air introduced into the first housing 21 is attached to the first inlet 23.

As illustrated in FIG. 4, a main flow passage 32 through which the air flows is defined in the first housing 21 of the main unit 20. In the main unit 20, an upstream end of the main flow passage 32 is connected to the first inlet 23. The blower 31 that feeds the air introduced through the first inlet 23 downstream is attached partway along the main flow passage 32. The blower 31 is, for example, a centrifugal fan. A first silencer 33 is attached between the first inlet 23 and the blower 31 in the main flow passage 32. The first silencer 33 attenuates a flowing sound of the air flowing through the main flow passage 32 due to drive of the blower 31.

A pressure sensor 34 that detects the pressure of the air on the downstream side relative to the blower 31 in the main flow passage 32 is attached inside the first housing 21. Furthermore, a flow amount sensor 35 that detects the flow amount of the air on the downstream side relative to the blower 31 in the main flow passage 32 is attached inside the first housing 21. Furthermore, a temperature sensor 36 that detects the temperature of the air flowing through the main flow passage 32 is attached inside the first housing 21. A first outlet unit 25 for discharging the air from the inside to the outside of the first housing 21 is connected to a downstream end of the main flow passage 32.

As illustrated in FIG. 1, the first outlet unit 25 projects from the first end surface 21A of the first housing 21. The first outlet unit 25 is disposed beside the first inlet 23 in the width direction Wd of the first housing 21. The entirety of the first outlet unit 25 has a cylindrical shape and projects from the first end surface 21A in the length direction Ld. An inner space of the first outlet unit 25 communicates with the main flow passage 32 inside the first housing 21.

The first outlet unit 25 is broadly divided into a small diameter portion 25A, a large diameter portion 25B, and a thin wall portion 25C in order from the first end surface 21A side. The inner diameter of the large diameter portion 25B is coincident with the inner diameter of the small diameter portion 25A, whereas the outer diameter of the large diameter portion 25B is greater than the outer diameter of the small diameter portion 25A. As a result, the outer circumferential surface of the small diameter portion 25A is recessed radially inward relative to the outer circumferential surface of the large diameter portion 25B. The outer diameter of the thin wall portion 25C is coincident with the outer diameter of the large diameter portion 25B, whereas the inner diameter of the thin wall portion 25C is greater than the inner diameter of the large diameter portion 25B. As a result, a level difference is formed at a boundary between the inner circumferential surface of the thin wall portion 25C and the inner circumferential surface of the large diameter portion 25B.

A first connector 27 for electrically connecting the main unit 20 and the base unit 40 to each other is recessed in the first end surface 21A. The first connector 27 is a so-called female connector and provided with a plurality of terminals therein. The first connector 27 is disposed below the first outlet unit 25.

Next, an electrical configuration in the main unit 20 of the CPAP device 10 is described.

As illustrated in FIG. 4, the main unit 20 includes a first controller 37 provided for controlling operation of the blower 31. The first controller 37 is electrically connected to the first connector 27 through wiring (not illustrated).

The first controller 37 can be configured as circuitry that includes 1) at least one processor that executes various processes in accordance with a computer program (software), 2) one or more dedicated hardware circuits such as an application-specific integrated circuit (ASIC) that execute at least a subset of various processes, or 3) a combination of 1) and 2). The processor includes a central processing unit (CPU) and memories, such as a random-access memory (RAM) and a read-only memory (ROM). The memories store program codes or instructions configured so as to cause the CPU to execute processes. Memories, that is, computer-readable media include any available media accessible to a general-purpose or dedicated computer.

A battery 38 for supplying the power to the blower 31, the pressure sensor 34, the flow amount sensor 35, the temperature sensor 36, and the first controller 37 are provided in the first housing 21 of the main unit 20. The battery 38 is a repeatedly rechargeable secondary battery. The battery 38 is recharged by connecting a recharging cable (not illustrated) to the main unit 20. The battery 38 is also electrically connected to the first connector 27.

A signal indicative of operation from the operation unit 22 is input to the first controller 37. A pressure value detected by the pressure sensor 34 is input to the first controller 37. A flow amount value detected by the flow amount sensor 35 is input to the first controller 37. A temperature value detected by the temperature sensor 36 is input to the first controller 37. The first controller 37 is configured such that the first controller 37 controls, based on these input values, the amount of the air to be fed or the like by increasing or decreasing the number of rotations of the blower 31 through control such as feed-back control or feed-forward control. For example, based on the detected values by the pressure sensor 34 and the flow amount sensor 35, the first controller 37 determines an inhaling state of the user and controls the pressure value of the air to be fed to the user so that the pressure value is synchronized with the inhaling state. The first controller 37 controls supplying of the power from the battery 38 to the first connector 27.

Next, the structure of the base unit 40 is described.

Figure 5:
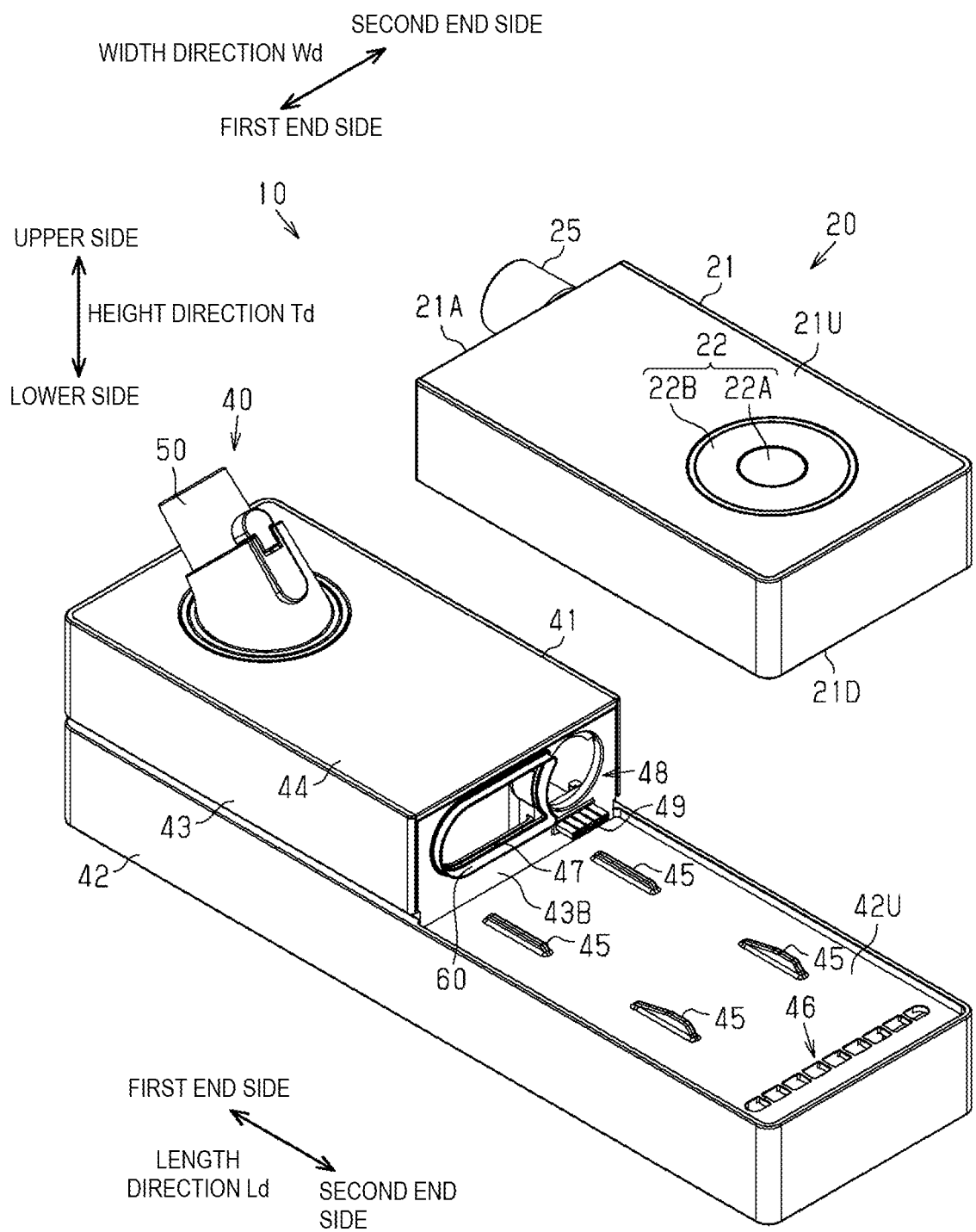
FIG. 5 is a perspective view of the CPAP device when seen in a different angle from the angle of FIG. 1.

As illustrated in FIG. 5, the base unit 40 includes a second housing 41 having an L-shape in side view. The second housing 41 is broadly divided into a base housing 42 having a flat box shape and a projecting housing 43 that is positioned on the upper side of the base housing 42 and has a flat box shape.

The dimension of the base housing 42 in the longitudinal direction is greater than the dimension of the first housing 21 in the length direction Ld. The dimension of the base housing 42 in the short-side direction is coincident with the dimension of the first housing 21 in the width direction Wd. In the following description, the longitudinal direction of the base housing 42 of the second housing 41 is assumed to extend along the length direction Ld of the first housing 21, and the short-side direction of the base housing 42 is assumed to extend along the width direction Wd of the first housing 21.

The projecting housing 43 projects from an upper surface on the first end side in the length direction Ld in the base housing 42. An end on the first end side in the length direction Ld in the projecting housing 43 is coincident with an end on the first end side in the length direction Ld in the base housing 42. The dimension of the projecting housing 43 in the height direction Td is substantially coincident with the dimension of the first housing 21 in the height direction Td. The dimension of the projecting housing 43 in the width direction Wd is substantially coincident with the dimension of the first housing 21 in the width direction Wd. The dimension of the projecting housing 43 in the length direction Ld is a value obtained by subtracting the dimension of the first housing 21 in the length direction Ld Td from the dimension of the base housing 42 in the longitudinal direction.

The base housing 42 and the projecting housing 43 each has a box shape having a cavity thereinside. The inner space of the base housing 42 and the inner space of the projecting housing 43 are continuous to each other. A wall portion of the projecting housing 43 opposite the base housing 42, that is, an upper wall portion, is configured as an openable lid 44. The lid 44 is made to be rotatable about the side on the first end side in the length direction Ld as a rotation center. In a state in which the lid 44 of the projecting housing 43 is rotated and opened, the inner space of the projecting housing 43 and part of the inner space of the base housing 42 are exposed.

An upper surface 42U of the base housing 42 is provided with projections 45 that project upward relative to the base housing 42 in the height direction Td. According to the present embodiment, two projections 45 per row are provided along the length direction Ld of the base housing 42. Regarding rows of the projections 45, two rows are provided in the width direction Wd of the base housing 42. That is, four of the projections 45 are provided in total.

Second inlets 46 for introducing the air from the outside to the inside of the base housing 42 are open in the upper surface 42U of the base housing 42. According to the present embodiment, a plurality of second inlets 46 are provided. The plurality of second inlets 46 are disposed so as to be arranged through a substantially entire region of the width direction Wd in the base housing 42. The second inlets 46 are each disposed near the edge on the second end side in the length direction Ld in the upper surface 42U of the base housing 42. Although the details will be described later, the upper surface 42U of the base housing 42 functions as a surface for placing the main unit 20.

As illustrated in FIG. 3, an upstream flow passage 53 through which the air sucked by the blower 31 of the main unit 20 flows is defined in the second housing 41 of the base unit 40. In the base unit 40, an upstream end of the upstream flow passage 53 is connected to the second inlets 46.

The second silencer 51 is attached partway along the upstream flow passage 53. The second silencer 51 attenuates a flowing sound of the air flowing through the upstream flow passage 53. The size of the volume of the second silencer 51 is greater than the volume of the first silencer 33 of the main unit 20, and a sound attenuation effect is higher with the second silencer 51 than with the first silencer 33 of the main unit 20.

A downstream end of the upstream flow passage 53 is connected to a second outlet 47 provided for guiding the air from the inside to the outside of the second housing 41. As illustrated in FIG. 5, the second outlet 47 is open in a surface connected to the upper surface 42U of the base housing 42 out of end surfaces on both sides in the length direction Ld of the projecting housing 43, that is, a second end surface 43B, which is a side surface on the second end side in the length direction Ld in the projecting housing 43. An opening shape of the second outlet 47 is the same as an opening shape of the first inlet 23 of the main unit 20.

Furthermore, as illustrated in FIG. 3, a downstream flow passage 54 through which the air fed by the blower 31 of the main unit 20 flows is defined in the second housing 41 of the base unit 40. The humidifier 52 is attached partway along the downstream flow passage 54. The humidifier 52 includes a container 52A, a heater 52B, and a heater temperature sensor 52C. The container 52A is configured such that the container 52A is detachable from the second housing 41 and allows water to be retained therein. The air is humidified when the air having introduced into the humidifier 52 is guided from the humidifier 52 through the inside of the container 52A. The heater 52B heats the water in the container 52A. The heater temperature sensor 52C detects the temperature of the heater 52B. According to the present embodiment, the container 52A of the humidifier 52 becomes detachable when the lid 44 of the projecting housing 43 of the second housing 41 is opened.

As illustrated in FIG. 5, a third inlet 48 for introducing the air from the outside to the inside of the projecting housing 43 is open in the second end surface 43B of the projecting housing 43 of the base unit 40. The third inlet 48 is disposed beside the second outlet 47 in the width direction Wd in the projecting housing 43. The third inlet 48 has a circular shape in plan view, and the outer diameter of the third inlet 48 is greater than the outer diameter of the first outlet unit 25 of the first housing 21.

A second connector 49 for electrically connecting the main unit 20 and the base unit 40 to each other projects in the second end surface 43B. The second connector 49 is a so-called male connector corresponding to the shape of the above-described first connector 27 and provided with a plurality of terminal therein. The second connector 49 is disposed below the third inlet 48.

A third outlet unit 50 that has a cylindrical shape and that is provided for guiding the air from the inside to the outside of the second housing 41 projects from the lid 44 of the second housing 41. The central axis line of the third outlet unit 50 is inclined related to the height direction Td in the projecting housing 43. An inner space of the third outlet unit 50 communicates with the downstream flow passage 54.

Next, an electrical configuration in the base unit 40 of the CPAP device 10 is described.

As illustrated in FIG. 3, the base unit 40 includes a second controller 56 that controls operation of the heater 52B. The second controller 56 can be configured as circuitry that includes 1) at least one processor that executes various processes in accordance with a computer program (software), 2) one or more dedicated hardware circuits such as an application-specific integrated circuit (ASIC) that execute at least a subset of various processes, or 3) a combination of 1) and 2). The processor includes a CPU and memories, such as a RAM and a ROM. The memories store program codes or instructions configured so as to cause the CPU to execute processes. Memories, that is, computer-readable media include any available media accessible to a general-purpose or dedicated computer.

The power is supplied from the battery 38 of the main unit 20 to the second controller 56 through the second connector 49 and the first connector 27 of the main unit 20. Also, a signal indicative of a temperature value of the air detected by the temperature sensor 36 is input from the first controller 37 to the second controller 56 through the second connector 49 and the first connector 27 of the main unit 20.

The second controller 56 sets a target heater temperature for heating the water in the container 52A based on the temperature value of the air having been input. For example, the second controller 56 sets the target heater temperature by using a predetermined calculation expression. The second controller 56 is configured such that the second controller 56 drives the heater 52B so as to make the heater temperature become the target heater temperature through control such as feed-back control or feed-forward control based on the heater temperature detected by the heater temperature sensor 52C. The second controller 56 adjusts the water temperature in the container 52A by using the heater 52B. When the heater temperature reaches the target heater temperature, the second controller 56 controls the heater 52B so as to maintain the heater temperature at the target heater temperature.

Here, the structure of a connection portion between the first inlet 23 of the main unit 20 and the second outlet 47 of the base unit 40 is described in detail.

Figure 6:
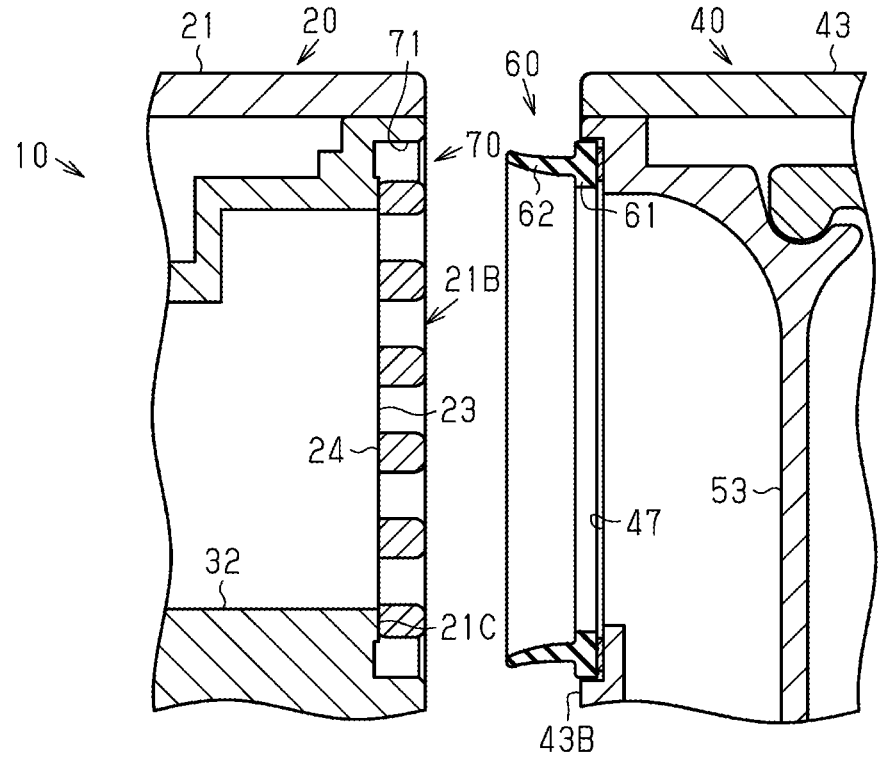
FIG. 6 is a partial sectional view illustrating a connection part between the first unit and the second unit.

As illustrated in FIG. 6, a sealing member 60 formed of rubber is secured to the second end surface 43B in the projecting housing 43 of the base unit 40. The sealing member 60 is disposed along the edge of the opening of the second outlet 47 to have an annular shape surrounding the second outlet 47 from outside. Furthermore, as a whole, the sealing member 60 extends from the second end surface 43B toward the second end side in the length direction Ld. According to the present embodiment, the base unit 40 is a secured-side unit to which the sealing member 60 is secured, and the main unit 20 is a partner-side unit to which the sealing member 60 is not secured.

The shape of the opening of the sealing member 60 at a distal end edge on the second end side in the extending direction, that is, the length direction Ld is such a shape that the sealing member 60 can surround the first inlet 23 of the main unit 20 from outside when the main unit 20 is attached to the base unit 40. Specifically, the opening shape of the sealing member 60 at the distal end edge on the second end side in the length direction Ld is similar to the opening shape of the first inlet 23 of the main unit 20 and has a greater opening area than that of the first inlet 23.

As illustrated in FIG. 6, the sealing member 60 includes a secured portion 61 secured to the second end surface 43B in the projecting housing 43 of the base unit 40 and a projecting portion 62 that extends from the secured portion 61 to the second end side in the length direction Ld. The secured portion 61 is secured to the projecting housing 43 with an adhesive. A securing portion where the secured portion 61 is secured to the second end surface 43B is a proximal end of the sealing member 60.

The secured portion 61 has an annular shape in which the dimension in the thickness direction is greater than the dimension in the extending direction. Furthermore, the dimension of the secured portion 61 in the thickness direction is uniform. The dimension of the sealing member 60 in the thickness direction is a dimension from an inner circumferential edge to an outer circumferential edge in a direction perpendicular to the opening surface of the sealing member 60 and the maximum thickness of the sealing member 60. That is, according to the present embodiment, the dimension of the sealing member 60 in the thickness direction is the dimension of the secured portion 61 in the thickness direction. The projecting portion 62 extends from a surface of the secured portion 61 on the second end side in the length direction Ld. The dimension of the projecting portion 62 in the thickness direction is smaller than the dimension of the secured portion 61 in the thickness direction. The dimension of the projecting portion 62 in the extending direction is greater than the dimension of the secured portion 61 in the thickness direction. Thus, the projecting portion 62 is deformable with respect to a direction perpendicular to the extending direction.

The shape of the projecting portion 62 is a tapered shape in which the opening area gradually decreases from the distal end to the proximal end in the extending direction. In other words, the projecting portion 62 has a shape in which, for example, outward warpage of the projecting portion 62 increases toward the distal end side in the extending direction. As a result, the opening area of the sealing member 60 at the distal end edge in the extending direction is greater than the opening area of the sealing member 60 at the proximal end in the extending direction. Regarding the entirety of the sealing member 60, according to the present embodiment, the dimension of the sealing member 60 in the extending direction is uniform and 2.0 times the dimension of the sealing member 60 in the thickness direction.

In the main unit 20, the filter 24 is attached to the first inlet 23. More specifically, a recessed portion 21B is recessed in the first end surface 21A of the main unit 20. The first inlet 23 is open in a recessed surface 21C, which is a bottom surface of the recessed portion 21B. In plan view, the filter 24 is slightly larger than the opening area of the first inlet 23 and is smaller than the opening area of the recessed portion 21B. An outer edge portion of the filter 24 is attached to the recessed surface 21C of the recessed portion 21B. In a state in which the filter 24 is attached to the first inlet 23, the outer edge of the filter 24 is spaced from the outer edge of the recessed portion 21B. As a result, a groove 70 recessed relative to the first end surface 21A is formed between the outer edge of the filter 24 and the outer edge of the recessed portion 21B.

In a state in which the main unit 20 is attached to the base unit 40, an outer circumferential surface of the recessed portion 21B, that is, an outer circumferential surface 71 of the groove 70 functions as a stopper surface. The outer circumferential surface 71 of the groove 70 faces the first inlet 23 side of the main unit 20. When seen in the length direction Ld, the outer circumferential surface 71 surrounds the second outlet 47 of the base unit 40 from outside. That is, the outer circumferential surface 71 of the groove 70 extends in a direction intersecting the opening surface of the first inlet 23.

Figure 7:
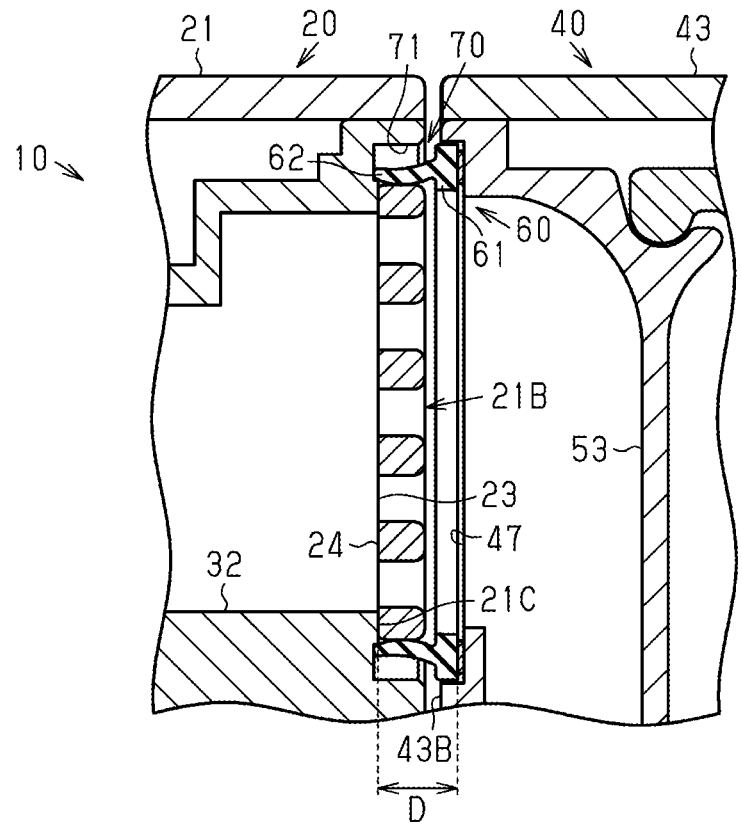
FIG. 7 is a partial sectional view illustrating the connection part between the first unit and the second unit.

As illustrated in FIG. 7, in the state in which the main unit 20 is attached to the base unit 40, a minimum distance D from the proximal end of the sealing member 60 in the extending direction to the main unit 20 is a minimum distance D between the securing portion of the sealing member 60 to the base unit 40 and the first end surface 21A of the first housing 21. The dimension of the sealing member 60 in the extending direction is greater than the minimum distance D. According to the present embodiment, the minimum distance D is set to 1.5 mm, and as the dimension of the sealing member 60 in the extending direction, 3.0 mm, that is, twice the minimum distance D is adopted.

Next, the operation of the CPAP device 10 in the first use state is described.

Figure 8:
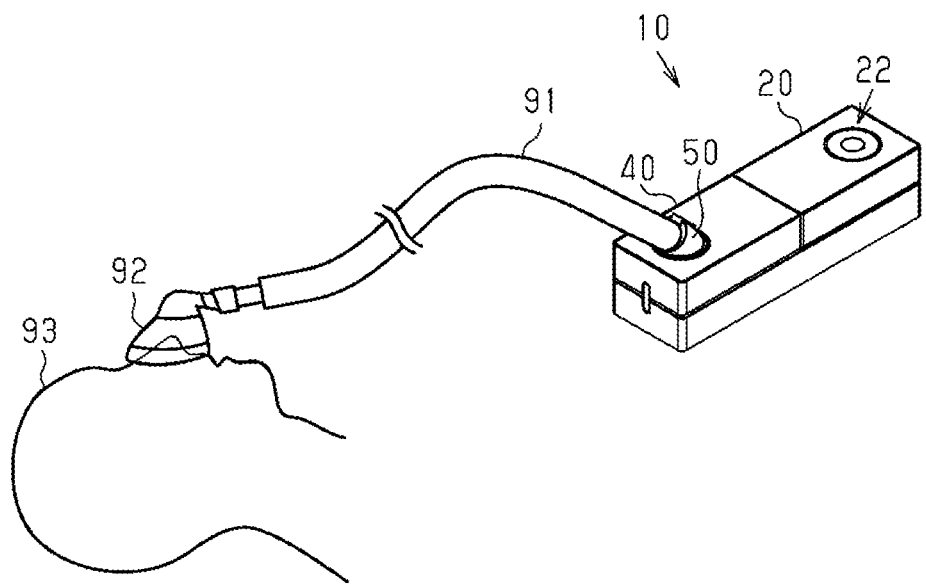
FIG. 8 is a schematic diagram illustrating the first use state of the CPAP device.

As illustrated in FIG. 8, in the first use state, the main unit 20 is attached to the base unit 40. Specifically, as illustrated in FIG. 2, the main unit 20 is placed on the base unit 40 such that a lower surface 21D of the first housing 21 faces the upper surface 42U of the base housing 42 in the second housing 41. Also, the first end surface 21A in the first housing 21 and the second end surface 43B of the projecting housing 43 in the second housing 41 face each other and are in contact with each other. Accordingly, in the first use state, the entirety of the CPAP device 10 has an elongated box shape.

As illustrated in FIG. 3, in the first use state, the first inlet 23 of the first housing 21 is connected to the second outlet 47 of the second housing 41, and, through the first inlet 23 and the second outlet 47, the upstream end of the main flow passage 32 of the main unit 20 is connected to the downstream end of the upstream flow passage 53 of the base unit 40. Also, the first outlet unit 25 of the first housing 21 is inserted into the third inlet 48 of the second housing 41, and, through the first outlet unit 25 and the third inlet 48, the downstream end of the main flow passage 32 of the main unit 20 is connected to the upstream end of the downstream flow passage 54 of the base unit 40.

As illustrated in FIG. 8, in the first use state, a first end portion of an air tube 91 is connected to the third outlet unit 50 of the base unit 40, and a second end portion of the air tube 91 is connected to a mask 92. The mask 92 is attached so as to, for example, cover the nose or mouth of a user 93.

In the first use state of the CPAP device 10, when the operation unit 22 of the main unit 20 is operated to turn on the power of the main unit 20, the blower 31 is driven. Here, with the projections 45 provided on the upper surface 42U of the base housing 42 of the base unit 40, a gap is formed between the lower surface 21D of the first housing 21 and the second inlets 46. Thus, the air is sucked into the CPAP device 10 through the second inlets 46 from this gap. The air having been sucked into the CPAP device 10 is guided from the third outlet unit 50 of the second housing 41 to the outside through the upstream flow passage 53 of the second housing 41, the main flow passage 32 of the first housing 21, and the downstream flow passage 54 of the second housing 41. Thus, the air is fed to the airway of the user 93 through the air tube 91 and the mask 92.

In the state in which the main unit 20 is attached to the base unit 40 as illustrated in FIG. 7, when the blower 31 is driven, the air to be sucked into the blower 31 flows through the main flow passage 32 and the upstream flow passage 53. The inside of a flow passage including the main flow passage 32 and the upstream flow passage 53 is placed under a negative pressure relative to the outside of the flow passage.

Accordingly, the projecting portion 62 of the sealing member 60 deforms toward the center of the first inlet 23 so as to fill a gap between the main unit 20 and the base unit 40.

Next, the CPAP device in the second use state is described.

Figure 9:
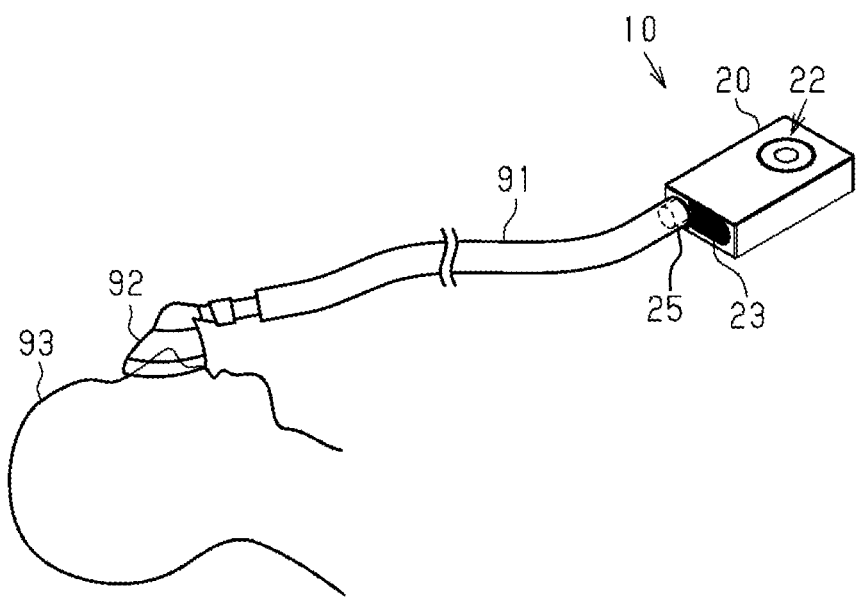
FIG. 9 is a schematic diagram illustrating the second use state of the CPAP device.

As illustrated in FIG. 9, in the second use state, the main unit 20 is not attached to the base unit 40, that is, the CPAP device 10 is used only with the main unit 20. In this case, the first end portion of the air tube 91 is connected to the first outlet unit 25 of the main unit 20, and the second end portion of the air tube 91 is connected to the mask 92. The mask 92 is attached so as to, for example, cover the nose or mouth of the user 93.

Next, the effects of the CPAP device 10 according to the above-described embodiment are described.

(1) According to the above-described embodiment, when the blower 31 of the main unit 20 is driven in the first use state in the CPAP device 10, due to the flow of the air flowing from the upstream flow passage 53 of the base unit 40 to the main flow passage 32 of the main unit 20, the pressure in these flow passages becomes a negative pressure relative to the atmospheric pressure. This negative pressure causes the sealing member 60 to deform so as to seal the gap between the main unit 20 and the base unit 40. Thus, in a state in which the blower 31 is driven, leakage of the air between the main unit 20 and the base unit 40 can be suppressed.

(2) According to the above-described embodiment, the opening area of the projecting portion 62 of the sealing member 60 increases toward the extending direction. This prevents the sealing member 60 from entering the first inlet 23 in the main unit 20 when the main unit 20 is attached to the base unit 40, and a configuration for surrounding the first inlet 23 of the main unit 20 from outside is easily achieved.

(3) According to the above-described embodiment, in the first use state, the distal end of the projecting portion 62 of the sealing member 60 in the extending direction is accommodated in the groove 70 before the blower 31 is driven. Thus, the distal end of the projecting portion 62 in the extending direction is easily positioned at an appropriate position. This decreases the likelihood of the occurrences of the following situation during attachment of the main unit 20 to the base unit 40: the distal end side of the projecting portion 62 excessively largely extends outward and ensuring of a close contact property fails rather than succeeds.

(4) According to the above-described embodiment, in the first use state, when the sealing member 60 deforms due to the negative pressure generated by driving of the blower 31, the inner circumferential surface of the projecting portion 62 is brought into surface contact into the inner circumferential surface of the groove 70. Thus, the close contact property between the projecting portion 62 and the groove 70 is easily improved.

(5) According to the above-described embodiment, the sealing member 60 is secured to the base unit 40. That is, in the second use state, the sealing member 60 is not disposed around the first inlet 23 of the main unit 20. Accordingly, when use in the second use state is assumed and the main unit 20 is carried, sealing member 60 is not contaminated or damaged.

(6) According to the above-described embodiment, regarding the dimension of the sealing member 60, the dimension of the sealing member 60 in the extending direction is 2.0 times the dimension of the sealing member 60 in the thickness direction. When the dimension of the sealing member 60 in the extending direction is excessively large, unintended deformation such as, for example, collapsing into a bellows shape may occur during attachment of the main unit 20 to the base unit 40. Thus, there is a possibility that the sealing member 60 is not appropriately brought into close contact with the base unit 40. When the dimension of the sealing member 60 in the extending direction is a dimension as in the above-described embodiment, the possibility of the occurrences of unintended deformation is low and, an appropriate close contact with the sealing member 60 is achieved.

(7) According to the above-described embodiment, the material of the sealing member 60 including the projecting portion 62 is rubber, and the projecting portion 62 elastically deforms. Thus, in the first use state, the sealing member 60 is easily deforms due to the negative pressure generated by drive of the blower 31.

The above-described embodiment may be modified and carried out as follows. The above-described embodiment and the following modifications may be combined and carried out without necessarily arising technical inconsistency.

In the above-described embodiment, the configuration of the main unit 20 is not limited to the example of the above-described embodiment. For example, the humidifier may be provided in the main unit 20.

In the above-described embodiment, the configuration of the base unit 40 is not limited to the example of the above-described embodiment. For example, the downstream flow passage 54 and the humidifier 52 may be omitted from the base unit 40. Furthermore, a function of adding fragrance or a medicinal component may be added to the humidifier 52 of the base unit 40. It is sufficient that the upstream flow passage 53 through which the air to be sucked into the blower 31 flows be defined in the base unit 40.

In the above-described embodiment, the shape of the first inlet 23 of the main unit 20 or the shape of the second outlet 47 of the base unit 40 is not limited to the example of the above-described embodiment. For example, the first inlet 23 may have a circular shape in plan view, whereas the second outlet 47 may have a quadrangular shape in plan view. Even when the shape of the first inlet 23 is not the same as the shape of the second outlet 47 as described above, it is sufficient that the first inlet 23 be able to be surrounded from outside by the distal end of the sealing member 60 in the extending direction.

In the above-described embodiment, the positional relationship between the first inlet 23 of the main unit 20 and the second outlet 47 of the base unit 40 is not limited to the example of the above-described embodiment. For example, when seen in the length direction Ld, the positions of the first inlet 23 and the second outlet 47 are not necessarily coincident with each other. In this case, regarding the size of the opening of the sealing member 60 at the distal end edge in the extending direction, the opening shape can be correspondingly increased so that the first inlet 23 can be surrounded from outside. Alternatively, the sealing member 60 may extend in an inclined direction toward the first inlet 23.

In the above-described embodiment, the shape of the sealing member 60 is not limited to the example of the above-described embodiment. For example, the secured portion 61 may be omitted. In this case, an end of the projecting portion 62 on the base unit 40 side can be secured to the second end surface 43B of the projecting housing 43 with an adhesive. As a result, the opening area of the projecting portion 62 included in the sealing member 60 decreases from the distal end toward the proximal end in the extending direction throughout the extending direction of the sealing member 60. The opening area may be uniform throughout the extending direction of the sealing member 60. It is sufficient that the sealing member 60 at least have a shape that is an annular shape surrounding the second outlet 47 from outside and that can surround the first inlet 23 from outside.

The dimension of the sealing member 60 in the extending direction is not limited to the example of the above-described embodiment. It is preferable that the dimension of the sealing member 60 in the extending direction be greater than or equal to 1.5 times and smaller than 6.0 times the dimension of the sealing member 60 in the thickness direction from the viewpoint of balance between ease of deformation of the sealing member 60 due to the negative pressure and suppression of unintended deformation of the sealing member 60 during attachment of the main unit 20 to the base unit 40.

The material of the sealing member 60 is not limited to the example of the above-described embodiment. For example, the material of the sealing member 60 may be an elastomer. In this case, as is the case with the example of the above-described embodiment, deformation of the sealing member 60 is easily achieved. In addition, the material of the sealing member 60 may be the same as the material of the first housing 21 and the second housing 41. Even in this case, when the dimension of the sealing member 60 in the thickness direction is correspondingly small, the sealing member 60 may deform due to the negative pressure generated by driving of the blower 31. As has been described, the material of the sealing member 60 can be appropriately selected depending on the shape of the sealing member 60 and the strength of the negative pressure generated by driving of the blower 31.

The securing portion of the sealing member 60 is not limited to the example of the above-described embodiment. For example, the sealing member 60 may be secured to the main unit 20. In this case, the main unit 20 is a secured-side unit to which the sealing member 60 is secured, and the base unit 40 is a partner-side unit to which the sealing member 60 is not secured.

The configuration of the groove 70 in the first end surface 21A of the main unit 20 is not limited to the example of the above-described embodiment. For example, the groove 70 may be a groove recessed in the first end surface 21A instead of configuring the groove 70 with the filter 24 and the recessed portion 21B. Furthermore, a surface of the groove 70 near the center in the first inlet 23 may be inclined so that the distance between the position of the surface and the center of the first inlet 23 decreases toward the second outlet 47. In this case, when the opening area of the projecting portion 62 of the sealing member 60 increases toward the distal end side in the extending direction, surface contact is easily achieved.

The stopper surface is not necessarily configured as the outer circumferential surface 71 of part of the groove 70. For example, in the above-described embodiment, the filter 24 is not necessarily provided. Even in this case, the outer circumferential surface of the recessed portion 21B functions as the stopper surface.

Although the above-described embodiment is configured such that the first outlet unit 25 of the main unit 20 is inserted into the third inlet 48 of the base unit 40, this projection/recess relationship may be reversed. That is, a structure corresponding to the third inlet 48 may be provided in the main unit 20, and a structure corresponding to the first outlet unit 25 may be provided in the base unit 40.

In the above-described embodiment, the battery may also be provided in the base unit 40. In the case where the battery is provided in the base unit 40, it may be allowed that the power is supplied from the battery of the base unit 40 to the battery 38 of the main unit 20 through the second connector 49 and the first connector 27 when the main unit 20 is attached to the base unit 40.

In the above-described embodiment, the sealing member 60 may be configured as, for example, a lip seal. The projecting portion 62 of the sealing member 60 may be configured as a lip having an annular shape or a loop shape.

In the above-described embodiment, the extending direction of the sealing member 60 may be referred to as a projecting direction of the projecting portion 62 of the sealing member 60. For example, the extending direction of the sealing member 60 may be parallel to or coincident with an air flow direction at a connection portion between the main flow passage 32 of the main unit 20 and the upstream flow passage 53 of the base unit 40. The air flow direction at this connection portion may be parallel to or coincident with the length direction Ld.

REFERENCE SIGNS LIST

10 CPAP device
20 main unit
21 first housing
21A first end surface
21B recessed portion
21C recessed surface
21D lower surface
21U upper surface
22 operation unit
22A switch
22B switch
23 first inlet
24 filter
25 first outlet unit
25A small diameter portion
25B large diameter portion
25C thin wall portion
27 first connector
31 blower
32 main flow passage
33 first silencer
34 pressure sensor
35 flow amount sensor
36 temperature sensor
37 first controller
38 battery
40 base unit
41 second housing
42 base housing
42U upper surface
43 projecting housing
43B second end surface
44 lid
45 projection
46 second inlet
47 second outlet
48 third inlet
49 second connector
50 third outlet unit
51 second silencer
52 humidifier
52A container
52B heater
52C heater temperature sensor
53 upstream flow passage
54 downstream flow passage
56 second controller
60 sealing member
61 secured portion
62 projecting portion
70 groove
71 outer circumferential surface
91 air tube
92 mask
93 user
D minimum distance

The invention claimed is:

1. A continuous positive airway pressure device configured to feed air to an airway of a user, the continuous positive airway pressure device comprising:
a first unit that includes a main flow passage through which the air is configured to flow and a blower in the main flow passage, and
a second unit that includes an upstream flow passage that is configured to be connected to an upstream of the main flow passage and that allows the first unit to be detachably attached to the second unit,
wherein said first unit further includes a first wall and said second unit includes a second wall, wherein said first and second walls are configured to face one another when the first unit is attached to the second unit,
wherein an outlet of the main flow passage projects from said first wall of said first unit, and an inlet is defined in the second wall of the second unit, wherein said outlet is configured to be inserted into and received within said inlet when the first unit is attached to the second unit,
wherein a sealing member that configured to seals a connection portion between the main flow passage and the upstream flow passage is secured to only one of the first unit and the second unit, wherein,
wherein the unit out of the first unit and the second unit to which the sealing member is secured is defined as a secured-side unit and the unit out of the first unit and the second unit to which the sealing member is not secured is defined as a partner-side unit,
wherein the sealing member has an annular shape that surrounds an opening of a flow passage of secured-side unit from outside, and a distal end side of the sealing member in an extending direction is configured to extend toward the partner-side unit when the first unit is attached to the second unit, wherein,
wherein a shape of an opening at a distal end edge of the sealing member in the extending direction has a shape that is configured to surround an opening of the flow passage of the partner-side unit from the outside when the first unit is attached to the second unit, wherein a dimension of the sealing member in the extending direction is greater than a dimension of the sealing member in a thickness direction, and the dimension of the sealing member in the extending direction is configured to be greater than a minimum distance from a proximal end of the sealing member in the extending direction to the partner-side unit when the first unit is attached to the second unit, and wherein the sealing member is disposed laterally adjacent to said outlet and said inlet when the first unit is attached to the second unit.

2. The continuous positive airway pressure device according to claim 1, wherein an opening area of the sealing member at the distal end edge in the extending direction is greater than an opening area of the sealing member at the proximal end in the extending direction.

3. The continuous positive airway pressure device according to claim 1, wherein the partner-side unit has a stopper surface that extends in a direction intersecting an opening surface of the flow passage of the partner-side unit and that faces an opening side of the flow passage of the partner-side unit, and wherein the stopper surface surrounds the opening surface of the flow passage of the partner-side unit from the outside.

4. The continuous positive airway pressure device according to claim 1, wherein the partner-side unit has a groove recessed in an opening surface of the flow passage of the partner-side unit, and wherein the groove surrounds the opening of the flow passage of the partner-side unit from the outside.

5. The continuous positive airway pressure device according to claim 1, wherein the secured-side unit is the second unit.

6. The continuous positive airway pressure device according to claim 1, wherein the dimension of the sealing member in the extending direction is greater than or equal to 1.5 times and smaller than 6.0 times the dimension of the sealing member in the thickness direction.

7. The continuous positive airway pressure device according to claim 1, wherein a material of the sealing member is rubber or an elastomer.

8. The continuous positive airway pressure device according to claim 2, wherein the partner-side unit has a stopper surface that extends in a direction intersecting an opening surface of the flow passage of the partner-side unit and that faces an opening side of the flow passage of the partner-side unit, and wherein the stopper surface surrounds the opening surface of the flow passage of the partner-side unit from the outside.

9. The continuous positive airway pressure device according to claim 2, wherein the partner-side unit has a groove recessed in an opening surface of the flow passage of the partner-side unit, and wherein the groove surrounds the opening of the flow passage of the partner-side unit from the outside.

10. The continuous positive airway pressure device according to claim 2, wherein the secured-side unit is the second unit.

11. The continuous positive airway pressure device according to claim 3, wherein the secured-side unit is the second unit.

12. The continuous positive airway pressure device according to claim 4, wherein the secured-side unit is the second unit.

13. The continuous positive airway pressure device according to claim 2, wherein the dimension of the sealing member in the extending direction is greater than or equal to 1.5 times and smaller than 6.0 times the dimension of the sealing member in the thickness direction.

14. The continuous positive airway pressure device according to claim 3, wherein the dimension of the sealing member in the extending direction is greater than or equal to 1.5 times and smaller than 6.0 times the dimension of the sealing member in the thickness direction.

15. The continuous positive airway pressure device according to claim 4, wherein the dimension of the sealing member in the extending direction is greater than or equal to 1.5 times and smaller than 6.0 times the dimension of the sealing member in the thickness direction.

16. The continuous positive airway pressure device according to claim 5, wherein the dimension of the sealing member in the extending direction is greater than or equal to 1.5 times and smaller than 6.0 times the dimension of the scaling member in the thickness direction.

17. The continuous positive airway pressure device according to claim 2, wherein a material of the sealing member is rubber or an elastomer.

18. The continuous positive airway pressure device according to claim 3, wherein a material of the sealing member is rubber or an elastomer.

19. The continuous positive airway pressure device according to claim 4, wherein a material of the scaling member is rubber or an elastomer.

20. The continuous positive airway pressure device according to claim 5, wherein a material of the sealing member is rubber or an elastomer.

21. The continuous positive airway pressure device according to claim 1, wherein the sealing member comprises a projecting portion having a tapered shape in which an opening area of the sealing member gradually decreases from the distal end edge of the sealing member to the proximal end of the sealing member in the extending direction.

* * * * *